United States Patent
Scheying et al.

(10) Patent No.: US 8,016,991 B2
(45) Date of Patent: Sep. 13, 2011

(54) POTENTIOMETRIC SENSOR DEVICE

(75) Inventors: Gerd Scheying, Stuttgart (DE); Jane Lewis, Wales (GB)

(73) Assignee: Robert Bosch GmbH, Stuttgart (DE)

( * ) Notice: Subject to any disclaimer, the term of this patent is extended or adjusted under 35 U.S.C. 154(b) by 816 days.

(21) Appl. No.: 10/825,571

(22) Filed: Apr. 15, 2004

(65) Prior Publication Data
US 2004/0238360 A1 Dec. 2, 2004

(30) Foreign Application Priority Data
Apr. 22, 2003 (DE) .................. 103 18 115

(51) Int. Cl.
G01N 27/403 (2006.01)

(52) U.S. Cl. ............. 204/433; 205/787.5; 324/438

(58) Field of Classification Search .......... 204/433, 204/280, 286.1, 290.14
See application file for complete search history.

(56) References Cited

U.S. PATENT DOCUMENTS

| | | | | |
|---|---|---|---|---|
| 1,956,741 A * | 5/1934 | Hornberger | ...................... | 127/48 |
| 3,726,777 A * | 4/1973 | Macur | ............................ | 600/347 |
| 3,843,400 A * | 10/1974 | Radford et al. | ............... | 429/152 |
| 4,582,589 A * | 4/1986 | Ushizawa et al. | ............. | 204/433 |
| 5,141,868 A | 8/1992 | Shanks et al. | | |
| 5,146,169 A * | 9/1992 | Morishita et al. | ............. | 324/438 |
| 5,215,643 A * | 6/1993 | Kusanagi et al. | ............. | 204/412 |
| 5,250,168 A * | 10/1993 | Tsukada et al. | ............... | 204/416 |
| 5,320,735 A * | 6/1994 | Kato et al. | ..................... | 204/419 |
| 5,522,980 A * | 6/1996 | Hobbs et al. | ................... | 204/432 |
| 5,869,007 A * | 2/1999 | Jang | ........................... | 422/82.02 |
| 5,904,987 A * | 5/1999 | Tani et al. | ..................... | 428/432 |
| 6,286,363 B1 * | 9/2001 | Discenzo | ..................... | 73/53.01 |
| 6,357,089 B1 * | 3/2002 | Koguchi et al. | ................. | 24/536 |
| 6,637,257 B2 * | 10/2003 | Sparks | .............................. | 73/38 |
| 2001/0005137 A1 * | 6/2001 | Horie et al. | ..................... | 324/438 |
| 2002/0113596 A1 * | 8/2002 | Horie et al. | ..................... | 324/438 |
| 2003/0047450 A1 | 3/2003 | Wang et al. | | |
| 2003/0089623 A1 * | 5/2003 | Peat et al. | ..................... | 205/775 |
| 2005/0014129 A1 * | 1/2005 | Cliffel et al. | ....................... | 435/4 |
| 2006/0073539 A1 * | 4/2006 | Wikswo et al. | ................. | 435/29 |

FOREIGN PATENT DOCUMENTS

| | | |
|---|---|---|
| DE | 44 30 662 | 3/1996 |
| DE | 195 44 690 | 6/1997 |
| DE | 196 12 680 | 10/1997 |
| DE | 100 62 044 | 6/2002 |
| GB | 2290617 | * 1/1996 |
| WO | WO 01/65248 | * 9/2001 |

* cited by examiner

*Primary Examiner* — Kaj K Olsen
(74) *Attorney, Agent, or Firm* — Kenyon & Kenyon LLP

(57) ABSTRACT

A potentiometric sensor device for measuring pH value is provided, which sensor device has two electrodes situated on a substrate and applied with the aid of thick-film technology. The two electrodes form an interdigital comb structure on the substrate. The interdigital comb structure allows the sensor device to be manufactured without a reference electrode having a glass body, so that the sensor device may easily be used where the sensor device is subjected to high mechanical loads.

20 Claims, 1 Drawing Sheet

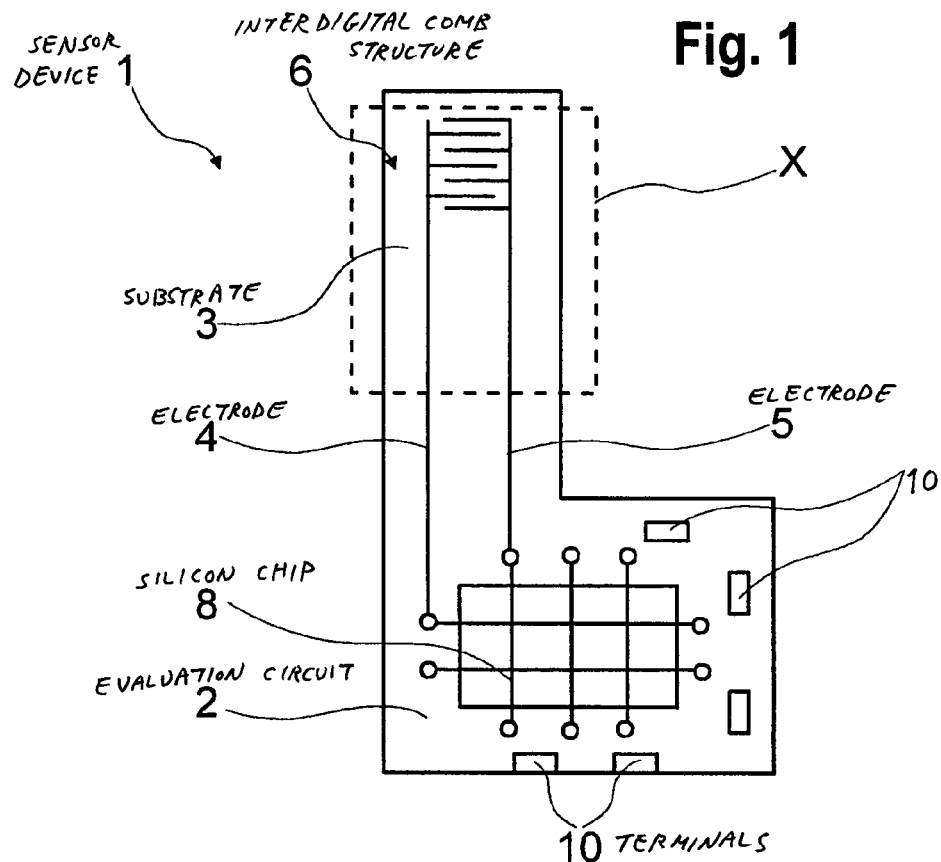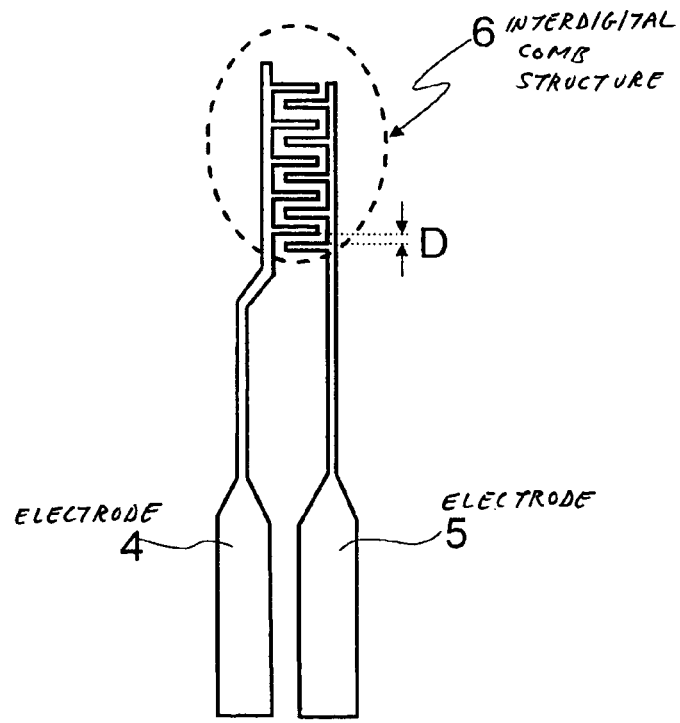
Fig. 1
Fig. 2 icon
POTENTIOMETRIC SENSOR DEVICE

FIELD OF THE INVENTION

The present invention relates generally to a potentiometric sensor device, and relates more particularly to a potentiometric sensor device for measuring pH values.

BACKGROUND INFORMATION

Conventional potentiometric sensors are based on the principle that, between at least two electrodes, an electrical voltage can be measured which changes with the change in the concentration of a chemical specimen. The voltage to be measured is produced by an electrical potential difference, which results from a difference in the chemical equilibrium potential of the individual electrodes with respect to their environment.

Such conventional sensors are used, for example, as oxygen sensors or as an electrochemical sulfuric acid cell for measuring carbon monoxide.

In addition, so-called gas electrodes or standard hydrogen electrodes are used for measuring acidic components in liquids or gases, i.e., for determining a hydrogen-ion concentration or a pH value, in mostly aqueous media. Furthermore, so-called diaphragm electrodes, such as a glass pH electrode or other solids having an ion-sensitive effect, are used for measuring pH values in liquid media.

In this context, however, the conventional potentiometric sensors used to measure pH values have the disadvantages of being costly to manufacture and having a low mechanical load-bearing capacity.

SUMMARY

The potentiometric sensor device according to the present invention for measuring pH values has the advantage over the conventional sensor devices in that the sensor device according to the present invention provides a very high structural integrity and is inexpensive to manufacture.

This is achieved in that the electrodes of the sensor device according to the present invention are applied to the substrate in an interdigital pattern, using thick-film technology, which means that the sensor device may be mass-produced. In addition, the interdigital structure allows the sensor device to be manufactured without a reference electrode having a glass body, so that the sensor device may easily be used where the sensor device is subjected to high mechanical loads, e.g., in automobiles and industrial equipment.

BRIEF DESCRIPTION OF THE DRAWINGS

FIG. 1 is a schematic diagram of a potentiometric sensor device according to the present invention, in the form of an oil-condition sensor having an evaluation circuit.

FIG. 2 is an enlarged view of region X shown in FIG. 1.

DETAILED DESCRIPTION

As shown in FIG. 1, an exemplary potentiometric sensor device 1, by which a pH value may be determined or measured in a liquid medium, is in the form of an oil-condition sensor having an evaluation circuit 2, by which an aging (i.e., degradation) process of a motor oil of a motor-vehicle engine may be detected, for example. In this manner, the condition of a motor oil may be continually monitored, and the time of a required oil change is ascertainable and displayable to a driver as a function of the actual condition of the motor oil.

As shown in FIG. 1, sensor device 1 has a substrate 3, on which two electrodes 4, 5 and an evaluation circuit 2 are situated. In this exemplary embodiment, substrate 3 takes the form of a ceramic foil made of a low-temperature-sintering, glass-ceramic substrate, e.g., a low-temperature cofiring ceramic (LTCC), which is characterized by a very low electrical conductivity and a very high mechanical strength. As an alternative, the substrate 3 may also be made of aluminum oxide, aluminum nitride, silicon dioxide, or a wafer of silicon, silicon nitride, or the like.

Using thick-film technology, the two electrodes 4 and 5 are applied to substrate 3 so as to have an interdigital comb structure or interdigital structure 6 (also shown in FIG. 2). Electrodes 4 and 5 are applied in the form of electrode-material pastes, using a screen-printing technique. The above-mentioned electrode pastes are made of the specific electrode material in powder form, and an inorganic or organic carrier material. During the manufacture of the pastes, the electrode-material powder is dispersed in the carrier material.

Depending on the type of screen used, electrodes having a layer height between 10 μm and 20 μm are applied to the substrate during the screen-printing procedure. The pasty electrodes, together with substrate 3, are subsequently fired in a firing process to produce a rigid connection between substrate 3 and the electrodes, and the carrier material of the pastes is evaporated, which in turn leads to a reduction in height of the layers.

As an alternative, the electrodes may be applied to the substrate with the aid of another known thick-film-technology printing method, such as stencil printing or foil printing, or using ink-jet technology.

To improve adhesion to substrate 3, the electrode materials initially present in powder form are each separately mixed with an inorganic powder, the inorganic powder presently corresponding to the substrate material. In this context, the inorganic material has constituents which melt during the firing process for producing the sensor device, and which constituents form a continuous material connection to the substrate with the aid of molecular forces between the molecules of the substrate and the inorganic material.

Depending on the specific application, the percentage of substrate material powder in the electrode paste is between 0.2 mass % and 20 mass %, and levels between 10 mass % and 15 mass % of inorganic powder, for example, achieves effective adhesion of electrodes 4 and 5 to substrate 3. Prior to application, the mixture of the electrode-material powder and the inorganic powder is mixed with the inorganic or organic carrier material or dispersed in the carrier material, the ratio of the carrier-material mass to the powder-mixture mass being set as a function of the specific application or printing technique, and the fraction of the electrode-material powder in the paste being between 10 mass % and 70 mass %.

The inorganic powder added to the electrode material to increase the adhesion of the electrodes to the substrate may also take the form of a glass ceramic, which is different from the substrate material and is made of a glass matrix and inert components intercalated in it, such as aluminum oxides or other suitable materials. In selecting the inorganic material, consideration needs to be given to balancing the effective adhesion of the electrodes to the substrate with the undesirable reduction in the conductivity of the electrodes by the inorganic material. The insulating effect of the inorganic material sets in after the sintering, since the material not only forms a continuous material connection to the substrate, but also at least partially surrounds the function particles of the electrodes as an insulating layer.

After application of the electrode pastes, substrate 3, along with electrodes 4 and 5 situated on it, is dried and sintered in a sintering process, and the carrier material previously mixed with the powder mixture is evaporated from the electrodes. During the sintering process, a highly rigid connection between electrodes 4, 5 and substrate 3 is produced, so that electrodes 4 and 5 safely remain on substrate 3, even in the case of high mechanical loads or vibrational loads.

If the substrate 3 is made of a low-temperature-sintering glass ceramic and electrodes 4 and 5 are made of iridium-oxide and/or silver pastes, then the sintering process is carried out at process temperatures less than 1000° C., e.g., at 950° C.

The sintering method and the selected material combination of the substrate and the electrodes are implemented in such a manner that substrate and electrode shrinkages occurring during the sintering process only differ from each other within a narrow range. This advantageously prevents the electrodes from peeling off the substrate and prevents cracks in the electrodes, which would otherwise occur if the shrinkage characteristics of the electrodes and the substrate are significantly different.

Electrode 4 shown in FIG. 1 is made of silver, and electrode 5 is made of iridium dioxide, for example. Alternative electrode materials suitable for manufacturing electrodes 4 and 5 include metals, such as platinum or rhodium, as well as oxides, such as iridium oxide, ruthenium dioxide, chromium trioxide, or iron trioxide. The utilized electrode materials are characterized by a certain electrical conductivity, so that the voltage does not drop too significantly over the measuring path and the internal resistance of the entire measuring cell is less than that of the measuring medium.

The structure of potentiometric sensor device 1 that results after the sintering process, i.e., consisting of silver electrode 4, iridium-dioxide electrode 5, and glass ceramic substrate 3, for example, is directly usable for measuring pH levels.

In an alternative embodiment according to the present invention, it is possible to treat the sensor device in an HCl or HBr bath, or in other halogenide ion baths, using an electrochemical oxidation process, in order to oxidize silver electrode 4 on its surface to form a silver halogenide and, therefore, to passivate it. This prevents or sharply reduces unwanted reactions of the pure silver electrode with the liquid, from which the pH value is sought to be measured. If the passivation layer of silver electrode 4 is a silver-chloride layer, then silver electrode 4 has a low material-exchange equilibrium with the surroundings, which means that a particularly resistant electrode is produced.

Iridium-dioxide electrode 5 does not change during the halogenation process for silver electrode 4 and continues to be present in unaltered form. Potentiometric sensor device 1 manufactured in this manner for measuring a pH value is characterized by a nearly ideal Nernst behavior (Delta_E=−0.059 V*pH), which means that very accurate measurements may be carried out without signal conversion.

If the sensor device of the present invention is used in non-liquid media, the electrode structure, i.e., the interdigital comb structure 6, which is shown in detail in FIG. 2 framed by a dotted line, is covered by a hydrous layer, i.e., a so-called coating. In principle, a number of polymers may be used for the coating, in particular polyamides such as PA 4, PA 4.4, PA 6, PA 6.6, PA 12, polyimide, polyacrylate, polyethylene glycol, or also celluloses and cellulose derivatives. A polymer gel, which is provided with water or other protic solvents such as alcohols, is generally used for the hydrous layer applied to the electrode structure.

If sensor device 1 having interdigital structure 6 and the hydrous layer situated on it is acted upon by a non-liquid medium, an equilibrium between the hydrogen-ion concentration in the coating and that of the non-liquid medium sets in at the boundary of the hydrous layer and the non-liquid medium, which means that an indirect measurement may be taken. Consequently, the sensor device of the present invention is particularly suitable for measuring the pH value in motor oil. In the case of motor oils, a so-called Total Base Number (TBN) or a so-called Total Acid Number (TAN) each represent technical synonyms for the pH value.

Since the measuring medium is a motor oil, the measurements may be desired to be taken at different operating states, e.g., at different motor-oil temperatures. Since the water content of the motor oil is a function of the temperature, the measured values ascertained by the sensor device of the present invention vary at different motor-oil temperatures. This may cause an evaluation of the measured values to assign different motor-oil qualities to the motor oil, although no change in the quality of the motor oil has effectively taken place. In order to circumvent this, it may be provided that the measured values ascertained by the sensor device of the present invention are corrected as a function of the current operating state, i.e., normalize the measurements, in order to be able to compare measured values of different operating states with each other. Such a procedure provides normalized measured values of the sensor devices of the present invention over the entire operating range of an internal combustion engine of a motor vehicle, such that the measured values reflect motor-oil qualitites independent of the measuring temperature.

Such compensation for the variable operating parameters, such as the water content of the motor oil that can vary over the operating states of an internal combustion engine, and hence the different operating temperatures of the motor oil, may be carried out by an appropriate evaluation circuit, which may be situated directly on the substrate of the sensor device.

In this context, the water content of the measuring medium may be either sensorially ascertained in a direct manner, via a conductivity determination, or determined as a function of measured values of a temperature-measuring device determining the current temperature of the motor oil, using characteristic curves stored in a data-storage medium associated with the sensor device.

The coating of sensor device 1 is made of an oil-resistant and, at the same time, hydrous polymer, so that the properties of the hydrous layer are not changed by contact with the motor oil over the service life of the internal combustion engine.

The hydrous layer may be applied to an electrode taking the form of a pure silver electrode, as well as to a passivation layer, e.g., on a halogenated surface of the silver electrode. In the case of the hydrous layer applied on a pure silver electrode, the hydrous layer likewise represents a passivation layer.

In the region of interdigital comb structures 6 of electrodes 4 and 5, the electrodes, which are applied to the substrate with the aid of thick-film technology, have spacing D between 0.1 μm and 1000 μm, as shown in FIG. 2. A spacing between 160 μm and 200 μm, e.g., 180 μm, produces good results when measuring the pH value in motor oil.

The two electrodes 4 and 5 are connected to a silicon chip 8 of evaluation circuit 2, the silicon chip being situated on substrate 3, as well, and being in contact with additional peripheral components of the evaluation circuit, such as resistors, capacitors, and the like, which are situated on substrate 3. In addition, the sensor device has terminals 10 for transmitting signals to an appropriate control unit of a motor vehicle, e.g., via a CAN bus.

During the operation of the sensor device according to the present invention, the two electrodes 4 and 5 generate potentiometric signals which are transmitted to an evaluation circuit. The evaluation circuit may take the form of an application-specific, integrated circuit (ASIC) which has a MOSFET input and an internal resistance of at least $10^{12}$ Ohm.

The sensor device according to the present invention may be implemented in such a manner that the sensing region of the sensor device, i.e., the region of the interdigital comb structures of electrodes 4 and 5, is positioned very near the evaluation circuit. This allows the voltage drop in the conductor tracks between the interdigital comb structures and the evaluation circuit to approach zero.

The glass ceramic used for producing substrate 3 is manufactured to have ceramic particles embedded in a glass matrix. On one hand, the embedded ceramic particles increase the thermal conductivity of the substrate and, on the other hand, cause the substrate to have a high E-modulus, as well as a sufficient hardness. The glass-ceramic glass matrix surrounding the ceramic particles electrically insulates the substrate very effectively and gives it a very low condensation temperature.

During a sintering process, which may involve a hot-pressing (also called pressure-sintering) techniques, the length and width of the above-described substrate remain largely unchanged, and only the height of the substrate is changed to a meaningful degree.

Using the sensor device of the present invention, a motor-oil change schedule may be continually adjusted as a function of the current condition of the motor oil, in contrast to the conventional method of relying on fixed oil-change intervals.

Therefore, the actual degradation state of the oil, which is a function of the operating conditions, may be taken into account for determining the optimum oil-change timing, thereby avoiding unnecessarily early oil changes, which impact the environment and result in an increase in the operating costs, as well as avoiding late oil changes which may negatively affect the engine operation and service life.

What is claimed is:

1. A potentiometric sensor device for measuring pH value, comprising:
    a substrate;
    two electrodes positioned on the substrate, wherein the two electrodes are applied with the aid of thick film technology, and wherein the two electrodes form an interdigital comb structure; and
    an evaluation circuit disposed on the substrate and in communication with the electrodes, the evaluation circuit configured to detect a degradation process of a motor oil based on the potentiometric response of the two electrodes and to ascertain a water content of the motor oil as a function of measured temperature values of the motor oil using characteristic curves stored in a data storage medium.

2. The potentiometric sensor device as recited in claim 1, wherein, in the region of the interdigital comb structure, the two electrodes have a spacing between 0.1 μm and 1000 μm.

3. The potentiometric sensor device as recited in claim 2, wherein the spacing between the two electrodes in the region of the interdigital comb structure is between 160 μm to 200 μm.

4. The potentiometric sensor device as recited in claim 3, wherein the substrate is made of a glass ceramic foil having a low electrical conductivity and a high mechanical strength.

5. The potentiometric sensor device as recited in claim 4, wherein the substrate is made of a low temperature sintering glass ceramic that cures at a temperature under 1000° C.

6. The potentiometric sensor device as recited in claim 5, wherein the two electrodes are made of at least one of metals and metallic oxides.

7. The potentiometric sensor device as recited in claim 6, wherein the two electrodes are made of at least one of silver and iridium dioxide.

8. The potentiometric sensor device as recited in claim 7, wherein at least one electrode is made of silver and has a silver halogenide layer on its surface in the region of the interdigital comb structure.

9. The potentiometric sensor device as recited in claim 4, wherein a hydrous layer made of a hydrous polymer is provided on the two electrodes.

10. The potentiometric sensor device as recited in claim 9, wherein the hydrous polymer is one of a polyamide and a polyimide.

11. The potentiometric sensor device as recited in claim 3, wherein a hydrous layer made of a hydrous polymer is provided on the two electrodes.

12. The potentiometric sensor device as recited in claim 11, wherein the hydrous polymer is one of a polyamide and a polyimide.

13. The potentiometric sensor device as recited in claim 1, wherein the two electrodes are applied to the substrate in the form of pastes, and wherein, in order to improve adhesion between the two electrodes and the substrate, the pastes include an inorganic material between approximately 0.2 mass % to 20 mass %.

14. The potentiometric sensor device as recited in claim 13, wherein the pastes include an inorganic material between approximately 10 mass % to 15 mass %.

15. The potentiometric sensor device as recited in claim 14, wherein the inorganic material corresponds to the substrate material.

16. The potentiometric sensor device as recited in claim 15, wherein the pastes are made of a powder mixture of electrode material and inorganic material, and a carrier material, the proportion of the powder mixture in the paste being between approximately 10 mass% and 70 mass%.

17. The potentiometric sensor device as recited in claim 14, wherein the pastes are made of a powder mixture of electrode material and inorganic material, and a carrier material, the proportion of the powder mixture in the paste being between approximately 10 mass % and 70 mass %.

18. The potentiometric sensor device as recited in claim 1, wherein a hydrous layer made of a hydrous polymer is provided on the two electrodes.

19. The potentiometric sensor device as recited in claim 18, wherein the hydrous polymer is one of a polyamide and a polyimide.

20. The potentiometric sensor device as recited in claim 1, wherein the evaluation circuit is further configured to normalize a measurement in response to different operating states of the motor oil.

* * * * *